United States Patent [19]

Boileau et al.

[11] Patent Number: 4,487,938

[45] Date of Patent: Dec. 11, 1984

[54] TETRANITROGLYCOLURIL AND METHOD OF PREPARATION THEREOF

[75] Inventors: Jacques Boileau, Paris; Jean-Marie L. Emeury, Sorgues; Jean-Paul Kehren, Angouleme, all of France

[73] Assignee: Societe Nationale des Poudres et Explosifs, Paris, France

[21] Appl. No.: 420,810

[22] Filed: Sep. 21, 1982

Related U.S. Application Data

[63] Continuation-in-part of Ser. No. 184,153, Sep. 4, 1980, abandoned, which is a continuation-in-part of Ser. No. 486,405, Jul. 8, 1974.

[30] Foreign Application Priority Data

Jul. 24, 1973 [FR] France ................. 73 27038

[51] Int. Cl.$^3$ .................. C07D 487/04; C06B 25/34; C06B 49/00
[52] U.S. Cl. .................... 548/304; 149/88; 149/92; 149/105; 149/109.4; 149/109.6; 260/688; 568/934
[58] Field of Search ............ 260/688; 423/393; 149/88, 92, 105, 109.4, 109.6; 568/934; 548/304

[56] References Cited

U.S. PATENT DOCUMENTS

| | | | |
|---|---|---|---|
| 2,400,287 | 5/1946 | Caesar | 260/688 |
| 2,435,314 | 2/1948 | Kokatnur | 260/688 |
| 2,594,588 | 4/1952 | Rothrock | 423/393 |
| 4,028,425 | 6/1977 | Gilbert | 423/393 |
| 4,211,874 | 7/1980 | Emeury et al. | 548/304 |

OTHER PUBLICATIONS

CA 98(4)-18921j, (1983).
CA 91(22)-177511x, (1979).
CA 89(26)-220969a, (1978).
CA 99(12)-90468e, (1983).
Kehren, J. P.; Soc. Natl. Poudres Explos., pp. 47-58, SNPE, Poudrerie de Sorques Vacluse, France, 1976.
Urbanski; Chemistry and Technology of Explosives, vol. 1, The Macmillan Co., N.Y., 1964.
Minsky, Picatinny Arsenal Memorandum Report No. MR-16, Jun. 27, 1952.

*Primary Examiner*—Teddy S. Gron
*Attorney, Agent, or Firm*—Bucknam and Archer

[57] ABSTRACT

The novel compound, tetranitroglycoluril, is described having a stability under vacuum of 6 cm$^3$/g/100 hours at 110° C. The compound exhibits a rate of detonation at least equal to 9,073 meters per second under a density charge of 1.94, has a decomposition temperature of about 200° C. and is stable at a temperature of up to 100° C. at normal pressure. It may be dried at 65° C. The brisance value by the Friedrich's formula is $159.7 \times 10^6$. The rate of detonation and brisance value are superior to octogen.

9 Claims, No Drawings

TETRANITROGLYCOLURIL AND METHOD OF PREPARATION THEREOF

This application is a continuation-in-part of U.S. Ser. No. 184,153 filed Sept. 4, 1980, now abandoned, which is a continuation-in-part of U.S. Ser. No. 486,405 filed July 8, 1974.

By definition, secondary explosives are substances which cannot detonate unless they are properly initiated, for instance by a primary explosive. Among the other pure secondary explosives, secondary crystalline high explosives are characterized by the facts that they are solid at room temperature, stable not only at room temperature but also at least at 100° C. and by the fact that they have a high brisance which supposes a high density and a high detonation rate.

Pentaerythrol tetranitrate or penthrite or PETN was first synthesized in 1894 and became available in proper state for use as an explosive by 1919.

Penthrite has a good thermal stability with regard to the other nitric esters. However, its thermal stability is lower than that of Hexogen or Octogen. It undergoes no decomposition below 100° C. since even under vacuum at 90° C. no more than 0.5 cm$^3$ of gases evolve from a one gram sample thereof, after 40 hours. Its decomposition begins only at 120° C. It melts with decomposition at 141° C. but its explosion temperature measured by heating at the rate of 5° C. per minute is 220° C.

The density of Penthrite is high. The crystal density (theoretical density) is 1.77 g/cm$^3$ but by compression, the maximum density reached with powdered penthrite is 1.74 g/cm$^3$. At the latter density, the rate of detonation is as high as 8,300 m/s.

Cyclotrimethylene trinitramine or RDX or Hexogen was first synthesized in 1916 by Brunswig (German Pat. No. 299,028) but its value as an explosive was only recognized by Von Herz in 1920 (British Pat. No. 145 791). It came into significant use only during World War II.

Hexogen has a very good thermal stability. It undergoes no decomposition below 100° C. It begins to decompose only at a temperature above 160°–170° C. Under vacuum and after 40 hours, only 0.2 and 0.8 cm$^3$ of gases evolve from a one gram sample of Hexogen at respectively 120° C. and 150° C. It melts with decomposition at 204° C. but its explosion temperature measured by heating at the rate of 5° C. per minute is 260° C.

The density of hexogen is very high. The crystal density (theoretical density) is 1.82 g/cm$^3$ at 20° C. but its highest practical density is only 1.72 g/cm$^3$. Its rate of detonation is 8,800 m/s at the theoretical density and 8,520 m/s at the highest practical density.

Cyclotetramethylenetetranitramine or HMX or octogen was only discovered and recognized as a valuable explosive during World War II.

Octogen has a very good thermal stability. It undergoes no decomposition below 100° C. It begins to decompose at a temperature higher than that of Hexogen. Under vacuum and after 40 hours only 0.08, 0.09, and 0.12 cm$^3$ of gases evolve from a one gram sample at respectively 100°, 120°, and 150° C.

It melts with decomposition at 280° C. but its explosion temperature measured by heating at the rate of 5° C. per minute is 330° C.

The density of octogen is one of the highest reported for a crystalline high explosive. The crystal density is 1.91 g/cm$^3$ at 20° C. for the β-stable crystalline form but the highest practical density obtained by compression of powdered octogen is 1.84 g/cm$^3$. At this density, its rate of detonation is 8,850 m/s.

In practice, hexogen and octogen are used at densities which are less than the crystal densities, and this is accompanied by a marked decrease in their rate of detonation.

The object of the present invention is to provide a novel compound, tetranitroglycoluril, which possesses valuable properties which enable it to be used as an explosive instead of and in place of hexogen or octogen.

Tetranitroglycoluril has the formula III hereinbelow:

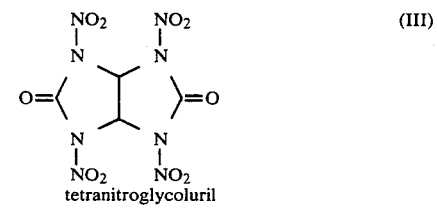

The substance is a very valuable crystalline high explosive. Tetranitroglycoluril has a good thermal stability since its thermal stability may be compared to that of penthrite. However, it outclasses penthrite and hexogen as to detonical properties. Only octogen approaches somewhat the detonical properties of tetranitroglycoluril. Tetranitroglycoluril undergoes no decomposition below 100° C. Under vacuum at 90° C., no more than 0.6 cm$^3$ of gases evolves from a one gram sample, after 40 hours.

At 60° C., its stability under vacuum is 0.5 and 1.2 cm$^3$/g after respectively 100 and 500 hours. At 75° C., after 100 hours only 0.8 cm$^3$ of gases has evolved from a one gram sample. At 90°, 100° and 110° C. and after 100 hours, the vacuum stability of tetranitroglycoluril is respectively 1.5, 3.2 and 6.0 cm$^3$/g. At 60° C., no gas evolution occurs between the end of the first hour and the 100th hour. Thése values of vacuum stability were obtained with the substance recrystallized from a mixture 1:1 methylene chloride-nitromethane However, we have found that the crude product, without recrystallization, is pure enough for all practical purposes. For instance, the crude product after 100 hours at 110° C. under vacuum only evolves 10 cc/g of gas, which shows that the substance is stable and the evolution of gas is linear, not exponential.

Tetranitroglycoluril, valuable as an explosive, is a white crystalline solid which has explosion temperature of 200° C., measured by differential thermal analysis, the heating being made at the rate of 5° C. per minute.

The actual density (theoretical or crystal density) of the unrecrystallized tetranitroglycoluril is 1.98 g/cm$^3$ at 25° C., measured in hexane with a pyknometer for solids. After recrystallization in nitromethane, the density is 2.02 g/cm$^3$ at 25° C. The highest practical density of tetranitroglycoluril obtained by compression is 1.98 g/cm$^3$. Tetranitroglycoluril detonates at a rate of 9,200 m/s at this density of 1.98 g/cm$^3$, which is superior to the crystal densities of Hexogen or Octogen. In view of the fact that in practice, hexogen and octogen are used at densities which are less than the crystal densities, and this is accompanied by a marked decrease in their rates of detonation, tetranitroglycoluril possesses valuable properties which enable it to be used as a secondary crystalline high explosive instead of and in place of hexogen or octogen.

The present invention also comprises a process for the preparation of tetranitroglycoluril, which comprises nitrating glycoluril or dinitroglycoluril with a mixture of nitric acid and dinitrogen pentoxide The mixture may be called "fuming nitric acid".

Glycoluril is a known compound which can, for example, be prepared by the condensation of glyoxal with urea and dinitroglycoluril is a known compound which can, for example, be prepared by the nitration of glycoluril. The preparation and properties of glycoluril and dinitroglycoluril are described, for example, in Beilstein, Handbuch der Organischen Chemie, vol XXVI, 4th Edition, page 443. The overall reaction scheme may, therefore, be shown as follows:

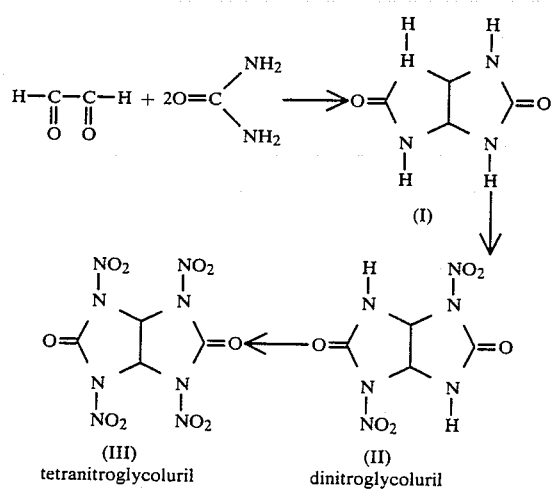

(III) tetranitroglycoluril
(II) dinitroglycoluril

The crude dinitroglycoluril obtained by nitration of glycoluril with nitric acid is mostly the 1,5-dinitro isomer. The impurity, which is probably the 1,3-isomer, may be removed by treatment with hot (90°-100° C.) water.

Dinitroglycoluril, used as an intermediate in the preparation of tetranitroglycoluril, is insoluble in water and nitromethane.

Conventional nitrating agents, for instance, nitric acid, $N_2O_5$, nitric acid together with sulfuric acid, with glycoluril or dinitroglycoluril do not form tetranitroglycoluril and it is necessary to use a mixture of nitric acid and dinitrogen pentoxide $N_2O_5$, which mixture is known as fuming nitric acid, in order to obtain the desired final product, tetranitroglycoluril.

In one embodiment of the process according to the invention, glycoluril is used as the starting material and is subjected to a conventional dinitration reaction employing nitric acid. The dinitroglycoluril obtained is then isolated and subjected to a second nitration step using fuming nitric acid, leading to tetranitroglycoluril.

In another embodiment of the process, glycoluril is nitrated directly by means of fuming nitric acid to form tetranitroglycoluril.

The value of the first embodiment arises from the well-known experimental fact that it is often preferred to carry out polynitration reactions in several steps in order to obtain products of improved quality.

In both cases, the fuming nitric acid used is preferably a mixture containing 5 to 50% by weight of dinitrogen pentoxide $N_2O_5$. With $N_2O_5$ contents of more than 50%, the nitrating bath becomes difficult to operate because of the difficulty of dissolving $N_2O_5$ in nitric acid at the working temperature. With a $N_2O_5$ content of less than 5%, the nitrating bath is no longer sufficiently active to effect the nitration within a reasonable period of time.

Nitration is effected by introducing glycoluril or dinitroglycoluril, which is preferably anhydrous, into fuming nitric acid, while keeping the temperature of the reaction mixture between −50° and +50° C. for the entire duration of the starting material introduction and of the subsequent reaction; this is facilitated by the fact that the nitration is only very slightly exothermic. At a temperature below −5° C., the reaction is very slow; above 50° C. secondary oxidation reactions become important and this leads to a reduction in the yield of the desired product.

A precipitate of tetranitroglycoluril appears gradually and increases with time. When precipitation is complete, the precipitate is filtered off, washed, for example with anhydrous methylene chloride, until neutral, and dried at about 65° C. to constant weight. Tetranitroglycoluril is very readily decomposed by water and other polar solvents even at a temperature of 10°-15° C. The substance is washed on the filter paper with an anhydrous inert solvent.

The filtrate resulting from the filtration step is collected and anhydrous methylene chloride is added to it. A second precipitate separates which is filtered off, washed with anhydrous methylene chloride until neutral and dried at about 65° C. to constant weight.

The overall yield of the crude product from the nitration process is of the order of 90%, whichever embodiment of the process is used.

The tetranitroglycoluril obtained has the following physical properties: it is a white crystalline solid which decomposes at a temperature of 200° C. (measured by differential thermal analysis). Its actual density, measured with a pyknometer for solids is 1.98 g/cm$^3$ at 25° C. The substance may be purified from dioxane, in which it is soluble to the extent of 17 g in 100 cc at 27° C. or from glacial acetic acid, in which it is soluble to the extent of 15.7 in 100 cc at 25° C.

Tetranitroglycoluril on infrared analysis exhibits bands at 1600 cm$^{-1}$, 1655 cm$^{-1}$, and 1625 cm$^{-1}$, which are attributable to the accumulation of four nitro groups in the same molecule.

In order that the invention may be more fully understood, the following examples are given by way of illustration only:

EXAMPLE 1

200 g of a mixture consisting of 79.6% of nitric acid and 20.4% (0.378 mol) of dinitrogen pentoxide, corresponding to nitric acid having a concentration of 103.4%, were introduced into a 350 cc reactor having two side tubes and provided with a stirrer, a thermometer and a reflux condenser. The mixture was cooled to +5° C. by means of a bath of iced water.

13.95 g of technical dinitroglycoluril (0.06 mol) were introduced in small amounts into the above mixture.

The temperature was kept below +10° C. for the entire duration of the running-in process. The dinitroglycoluril dissolved slowly in the nitrating bath as it was added, the addition being carried out over the course of 30 minutes. At the end of the addition, the reaction mixture was clear. It was left for two hours at +10° C., with stirring, in order to complete the reaction.

After stirring for approximately 30 minutes, a precipitate appeared which increased with time. When precipitation was complete, the precipitate was filtered off, washed on the filter with anhydrous methylene chloride until neutral, and dried in an oven at 65° C. to constant weight.

15.9 g of dry tetranitroglycoluril was thus obtained, corresponding to a yield of 82.3%. The nitrogen content of the product was 16.8% (theory=17.39); the purity was thus 96.6%.

A second crop was recovered by adding 200 cc of anhydrous methylene chloride to the above filtrate. A precipitate appeared very slowly which was collected on the filter, washed with methylene chloride until neutral and dried at 65° C.

1.45 g of dry tetranitroglycoluril, with a nitrogen content of 16.97%, corresponding to a purity of 97.6%, were thus obtained.

The overall yield of the nitration process was 90%.

EXAMPLE 2

100 g of a mixture consisting of 56.2% of nitric acid and 43.8% of dinitrogen pentoxide, corresponding to nitric acid having a concentration of 107.2%, were introduced into the same reactor as in the preceding example. The mixture was cooled to between 0° and +3° C., and 2.84 g (0.02 mol) of recrystallized glycoluril were then introduced over the course of three minutes, whilst keeping the temperature between 0° and +3° C.

A precipitate appeared after 30 minutes and the reaction was complete after two hours during which time the temperature did not rise above +10° C.

The precipitate was then filtered off at this temperature and the product collected was washed on the filter with anhydrous methylene chloride until neutral. 5.4 g of the tetranitroglycoluril were obtained, after drying to constant weight in an oven at 65° C.

A second crop was recovered by adding 200 g of methylene chloride to the above filtrate. A precipitate appeared very slowly and was filtered off and washed until neutral with methylene chloride. After drying at 65° C., 0.3 g of tetranitroglycoluril was obtained.

The overall yield of the nitration process was 88.5%.

The use of tetranitroglycoluril as an explosive with a high rate of detonation is illustrated by the following example where two detonating fuses are prepared, the one charged with tetranitroglycoluril and the other with octogen.

EXAMPLE 3

Following the conventional technique for manufacturing detonating fuses by stretching, a detonating fuse was prepared by charging a silver sheath with tetranitroglycoluril and then stretching the loaded sheath. The characteristics of the fuse obtained were as follows:
  external diameter: 4 mm
  linear weight: 119.00 g/m
  linear explosive charge: 2.81 g/m
  charge density: 1.94

The rate of detonation of this fuse was 9,073 meters per second.

By way of comparison, a similar detonating fuse was made using octogen instead of tetranitroglycoluril; stretching was carried out in an absolutely identical manner.

The characteristics of the fuse were as follows:
  external diameter: 4 mm
  linear weight: 101.00 g/m
  linear explosive charge: 6.21 g/m
  charge density: 1.72

The rate of detonation of the fuse containing octogen was 8,631 meters per second.

It is thus seen that tetranitroglycoluril enables detonating fuses to be manufactured which have greater rates of detonation and charge densities than those of otherwise similar fuse containing octogen.

The value of tetranitroglycoluril as an explosive substance in general derives from the fact that it combines:

(i) a very high theoretical rate of detonation, at least equal to 9,100 meters per second, (ii) a density of 1.98 g/cc, which is greater than that of octogen and hexogen, the density of octogen $\beta$ and hexogen crystals being, under the same conditions, 1.907 and 1.816 at 20° C., (iii) a high melting point and decomposition temperature, equal to 200° C., and (iv) a better oxygen balance than that of hexogen and octogen.

The impact sensitivity is 0.19 kgm and the friction sensitivity 7 kgf, measured by the Julius Peters equipment, in accordance with the method described by H. D. Mallory (the development of impact sensitivity tests at the Explosive Research Laboratory, Bruceton, Pa. during the years 1941–1945, U.S. Naval Ordinance Lab., White Oak, Md., 1956, Report 4236).

BRISANCE VALUE

The brisance value measures the ability of an explosive to demolish or fragment a solid object. This value may be easily calculated according to Friedrich's formula, according to which $$B = D^2\text{max} \times \text{density}$$

Many methods have been used to determine the brisance value. According to the Friedrich formula, one needs to know the density of the explosive ($\Delta$) and the maximum detonation velocity (D max). The density has been determined, $\Delta = 1.94$ g/cm$^3$. D max = 9,073 m/s is a minimum value of the rate of detonation. Thus, $(9073)^2 \times 1.94 = 159.7 \times 10^6$, which is the minimum brisance value. This value is higher than hexogen for which a value of $114.6 \times 10^6$ has been reported and even octogen which gives $153.2 \times 10^6$. Penthrite (PETN) has a value of only $117.1 \times 10^6$.

By way of comparison, the values obtained for tetranitroglycoluril, penthrite (pentaerythritol tetranitrate), hexogen and octogen are:

|  | Tetranitroglycoluril | Hexogen | Octogen | Penthrite |
|---|---|---|---|---|
| Impact Sensitivity in kgm | 0.19 | 0.45 | 0.52 | 0.31 |
| Friction Sensitivity in kgf | 7 | 11.5 | 10 | 4.5 |
| Brisance Value by the Friedrich's formula | $\geq 159.7 \times 10^6$ | $114.6 \times 10^6$ | $153.2 \times 10^6$ | $117.1 \times 10^6$ |

Tetranitroglycoluril can be employed in the majority of cases where hexogen and octogen are used and, in particular:

(i) as an explosive charge in the form of the pure compound, (ii) as an explosive charge when mixed with a compound which makes charging possible in the molten state, such as trinitrotoluene, (iii) as an explosive charge when mixed with a polymerisable liquid plastic binder, which enables charging to be effected by casting, (iv) as an explosive charge when mixed either with waxes or more generally with thermoplastic materials which make charging possibly by compression, (v) as an explosive charge when mixed with phlegmatising products, and (vi) as an oxidizing charge in solid propellants.

It can be used for the production of relay explosives and detonating fuses and is particularly suitable for the preparation of explosive charges on any occasion when it is desired to liberate the maximum energy for a given volume.

What is claimed is:

1. Tetranitroglycoluril having a rate of detonation at least equal to 9073 meters per second under a density charge of 1.94, having a decomposition temperature of about 200° C. which is stable at a temperature of up to 100° C. and is soluble in dioxane to the extent of 17 g in 100 cc at 27° C. and in acetic acid to the extent of 15.7 in 100 cc at the temperature of 25° C.

2. Tetranitroglycoluril according to claim 1 wherein the stability under vacuum is 0.8 $cm^3/g$/100 hours at 75° C. and at 110° C. is 6 cc $cm^3/g$/100 hours.

3. Tetranitroglycoluril according to claim 1 or 2 which exhibits a sensitivity to mechanical impact of 0.19 Kgm measured by the Julius Peter's apparatus.

4. Tetranitroglycoluril according to claim 1 or 2 which exhibits a brisance value of $159.7 \times 10^6$ measured by Friedrich method.

5. Tetranitroglycoluril according to claim 1 which exhibits on infrared analysis bands at 1655 $cm^{-1}$, 1625 $cm^{-1}$, and 1600 $cm^{-1}$.

6. A process for the preparation of tetranitroglycoluril, which consists of nitrating a starting material selected from the group consisting of glycoluril and dinitroglycoluril with a mixture of nitric acid and dinitrogen pentoxide at a temperature between −5° C. and 50° C., allowing the product to precipitate and filtering the product from the reaction mixture.

7. A process according to claim 6, wherein nitration is effected at a temperature of from about 0° C. to about +10° C.

8. A process according to claim 5 wherein said mixture contains from 5 to 50% by weight of dinitrogen pentoxide.

9. A process for the preparation of tetranitroglycoluril, which consists of nitrating a starting material selected from the group consisting of glycoluril and dinitroglycoluril with a mixture of nitric acid and dinitrogen pentoxide at a temperature between −5° C. and 50° C., allowing the product to precipitate, filtering the product from the reaction mixture and washing the product with an inert anhydrous solvent.

* * * * *